United States Patent
Okawa

[11] Patent Number: 6,013,822
[45] Date of Patent: Jan. 11, 2000

[54] METHOD FOR THE PREPARATION OF HIGH-PURITY METHACRYLOXYPROPYLDIMETHYLCHLOROSILANE

[75] Inventor: Tadashi Okawa, Chiba Prefecture, Japan

[73] Assignee: Dow Corning Toray Silicone Co., Ltd., Tokyo, Japan

[21] Appl. No.: 08/734,288

[22] Filed: Oct. 21, 1996

[30] Foreign Application Priority Data

Nov. 21, 1995 [JP] Japan ................................ 7-326502

[51] Int. Cl.$^7$ ........................................................ C07F 7/08
[52] U.S. Cl. .............................................................. 556/440
[58] Field of Search .............................................. 556/440

[56] References Cited

U.S. PATENT DOCUMENTS

| | | | |
|---|---|---|---|
| 2,386,488 | 10/1945 | McGregor | 260/607 |
| 4,946,977 | 8/1990 | Bernhardt et al. | 556/440 |
| 4,985,579 | 1/1991 | Bokerman | 556/466 |
| 5,117,027 | 5/1992 | Bernhardt et al. | 556/440 |

FOREIGN PATENT DOCUMENTS

| | | |
|---|---|---|
| 556802A1 | 8/1993 | European Pat. Off. . |
| 562584A1 | 9/1993 | European Pat. Off. . |

OTHER PUBLICATIONS

Bulletin of the Chemical Society of Japan, vol. 57, No. 5, May 1984, pp. 1431–1432.

Bulletin of the Academy of Sciences of USSR. Division of Chemical Science, vol. 38, No. 3, Part 02, Mar. 1, 1989, pp. 597–600.

Cameron, G. et al.; Polymer, 1985, vol. 26, pp. 437–442, "Polymerization of poly(dimethylsiloxane) macromers: 1. Copolymerization with styrene".

*Primary Examiner*—Paul F. Shaver
*Attorney, Agent, or Firm*—Alex Weitz

[57] ABSTRACT

A method for preparing high-purity methacryloxypropyi-dimethylchlorosilane is disclosed, said method comprising mixing (A) a methacryloxypropyldimethylchlorosilane which contains an Si-bonded methacryloxy-functional organosilicon compound as an impurity with (B) an inorganic chloride, reacting said inorganic chloride with said Si-bonded methacryloxy- functional organosilicon compound and thereafter isolating the methacryloxypropyldim-ethylchlorosilane.

10 Claims, No Drawings

METHOD FOR THE PREPARATION OF HIGH-PURITY METHACRYLOXYPROPYLDIMETHYLCHLOROSILANE

FIELD OF THE INVENTION

This invention relates to a method for the preparation of high-purity methacryloxypropyldimethylchlorosilane and more particularly to a preparative method that yields a high-purity methacryloxypropyidimethylchlorosilane that contains little Si-bonded methacryloxy-functional organosilicon compound as impurity.

BACKGROUND OF THE INVENTION

Methacryloxy-functional organosilicon compounds readily react with radically polymerizing monomers such as methyl methacrylate and styrene, and for this reason are used as starting materials for copolymers deriving from these monomers and as modifiers for polymers prepared from the aforesaid monomers.

Among the methacryloxy-functional organosilicon compounds, methacryloxypropyldimethylchlorosilane is used as an endblocker or terminating agent for methacryloxy-functional silicone macromonomers. Methacryloxypropyldimethylchlorosilane has been prepared by an addition reaction between allyl methacrylate and dimethylchlorosilane followed by isolation by distillative purification of the resulting methacryloxypropyidimethylchlorosilane from the reaction mixture (refer to, for example, *Polymer*, Volume 26, page 437, 1985).

SUMMARY OF THE INVENTION

It has now been found that Si-bonded methacryloxy-functional organosilicon compounds occur as impurities in the methacryloxypropyidimethylchlorosilane afforded by the above mentioned method. This can cause problems such as, for example, a reduced copolymerization conversion in the reaction of radically-polymerizable vinyl compounds with methacryloxy-functional silicone macromonomer prepared using such methacryloxypropyldimethylchlorosilane as endblocker. The inventor also discovered that a very pure methacryloxypropyldimethylchlorosilane containing very low levels of these impurities can be prepared by using a special class of inorganic chlorides to treat methacryloxypropyldimethylchlorosilane contaminated with Si-bonded methacryloxy-functional organosilicon compound and by following this treatment with distillative purification. The present invention was achieved based on these discoveries.

In specific terms, then, the object of the present invention is to provide a highly productive method for the preparation of high-purity methacryloxypropyldimethylchlorosilane contaminated by only small amounts of Si-bonded methacryloxy-functional organosilicon compound.

The present invention, therefore, relates to a method comprising mixing (A) a methacryloxypropyldimethylchlorosilane containing an Si-bonded methacryloxy-functional organosilicon compound as impurity with (B) an inorganic chloride sand reacting the inorganic chloride with the Si-bonded methacryloxy-functional organosilicon compound and thereafter isolating the methacryloxypropyldimethylchlorosilane.

The present invention has been disclosed in Japanese Patent Application Number Hei 07/326502, the full disclosure of which is hereby incorporated by reference.

DETAILED DESCRIPTION OF THE INVENTION

To explain the preceding in greater detail, the methacryloxypropyldimethylchlorosilane (A) used by the present invention can be prepared by those methods known in the art. For example, it can be obtained by an addition reaction between allyl methacrylate and dimethylchlorosilane in the presence of a platinum catalyst (refer to, for example, *Polymer*, Volume 26, page 437, 1985). This methacryloxypropyldimethylchlorosilane generally contains at least Si-bonded methacryloxy-functional organosilicon compound as an impurity. The following structures are examples of Si-bonded methacryloxy-functional organosilicon compounds that can be present as impurities.

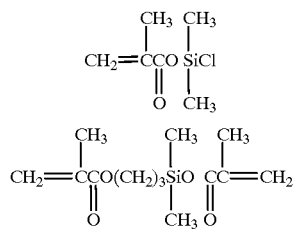

The inorganic chloride (B) used by the present invention reacts with the Si-bonded methacryloxy-functional organosilicon compound present as impurity in component (A) and thereby converts the silicon-acyloxy bond into a silicon-chlorine bond. The subject inorganic chloride is specifically exemplified by thionyl chloride, phosphoryl chloride, phosphorus pentachloride, phosphorus trichloride, and boron trichloride, wherein thionyl chloride is preferred among these examples.

The reaction between the Si-bonded methacryloxy-functional organosilicon compound present in the methacryloxypropyldimethylchlorosilane and the inorganic chloride is preferably run using the inorganic chloride at least at equivalency with reference to the Si-bonded methacryloxy-functional organosilicon compound. The reaction is preferably run in the absence of solvent, but can be run in the presence of solvent. The solvent is exemplified by aromatic solvents such as benzene, toluene, xylene, and so forth, and by aliphatic solvents such as hexane, heptane, and so forth. Moreover, the addition reaction between allyl methacrylate and dimethylchlorosilane can be run in such a solvent and the reaction with inorganic chloride can then also be run directly in the same solvent without an intervening work up. The reaction under consideration can be run at room temperature, but reaction rate considerations generally make it advantageous to run the reaction at from 50° C. to 200° C.

The SiCl-functional compounds obtained from the Si-bonded methacryloxy-functional organosilicon compounds according to the present method have low boiling points and can therefore be easily eliminated in the ensuing purification process. This purification process can use those purification techniques known in the art, but purification by distillation will generally be used. The preliminary addition of a polymerization inhibitor is recommended in the present invention in order to prevent polymerization reactions of the methacryloxy group that can occur as secondary reactions during distillative purification. Said polymerization inhibitor is exemplified by phenothiazine, hindered phenol compounds, amine compounds, quinone compounds, and the like. However, the nature and quantity of the polymerization inhibitor are not critical as long as addition of the polymerization inhibitor can prevent methacryloxy group polymerization during distillative purification. In addition, the preparative method provided by the present inventor and others in Japanese Patent Application Laid Open Number Hei 5-271248 (271,248/1993) is also recommended as an excellent method that inhibits polymerization of the methacryloxy group. This method involves the addition of metal halide to the distillative purification.

EXAMPLES

The invention is explained below using working examples, but the invention is not limited to these examples.

Example 1

Allyl methacrylate, (64.9 g; 513 mmol)) 30 g of n-hexane, and 0.41 g of phenothiazine were mixed and the mixture was azeotropically dried by heating under reflux for 1 hour. A platinum-1,3-divinyltetramethyldisiloxane complex was added with mixing in a quantity sufficient to give 20 ppm of platinum metal referred to the amount of allyl methacrylate. The mixture was then heated to 70° C. with stirring and a small amount of dimethylchlorosilane was added dropwise. After confirmation of initiation of the addition reaction and while maintaining the temperature at 60° C. to 75° C. through air or water cooling, a reaction was run by adding 32.3 g (342 mmol) of dimethylchlorosilane dropwise and stirring for 30 minutes. This yielded a reaction mixture of methacryloxypropyldimethylchlorosilane. Cupric chloride (0.75 g) and 2 g (17.1 mmol) of thionyl chloride were then added followed by heating under reflux at 70° C. for 2 hours. The low-boiling substances were thereafter distilled from the reaction mixture under reduced pressure. This was followed by distillation at a vacuum of 10 mmHg, during which the fraction at 116° C. to 120° C. was collected. The results of various analyses confirmed this fraction to be methacryloxypropyldimethylchlorosilane. In particular, $^{29}$Si-NMR (nuclear magnetic resonance) analysis indicated very low integrated strength ratios for the signals at 23.7 ppm and 19.4 ppm assigned to the Si-bonded methacryloxy-functional organosilicon impurity compounds given below (Table 1). This confirmed a low content for these impurities.

TABLE 1

| chemical shift | content (mol %) |
|---|---|
| 23.7 ppm[1] | 0.08 |
| 19.4 ppm[2] | 0 |

[1] 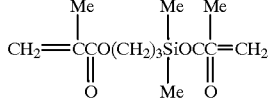

[2] 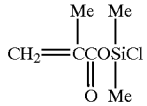

Example 2

An addition reaction was run as in Example 1 to obtain a reaction mixture of methacryloxypropyldimethylchlorosilane. After completion of the addition reaction, a 2 g sample of the reaction mixture was removed and measured by $^{29}$Si-NMR in order to determine the content of Si-bonded methacryloxy-functional organosilicon impurity. Another 2 g sample of this reaction mixture was also taken and combined with 0.12 g (1.02 mmol) of thionyl chloride, heated for 1 hour at 70° C. with stirring, and then submitted to measurement by $^{29}$Si-NMR in order to determine the content of Si-bonded methacryloxy-functional organosilicon inpurity. The results confirmed that the treatment with thionyl chloride had reduced the content of Si-bonded methacryloxy-functional organosilicon compounds. This thionyl chloride-treated reaction mixture was distilled under reduced pressure (in the presence of cupric chloride) as in Example 1 to give methacryloxypropyidimethylchlorosilane. $^{29}$Si-NMR analysis confirmed that this methacryloxypropyidimethylchlorosilane contained little or no Si-bonded methacryloxy-functional organosilicon impurity. The results are reported in Table 2.

TABLE 2

| | content (mol %) | |
|---|---|---|
| chemical shift | untreated | treated with thionyl chloride |
| 23.7 ppm | 1.67 | 0 |
| 19.4 ppm | 2.60 | 1.61 |

Comparative Example 1

A reaction was run as in Example 1 to yield a reaction mixture of methacryloxypropyldimethylchlorosilane. After completion of the addition reaction, a distillative purification was run with the addition of 0.75 g cupric chloride but without the treatment with thionyl chloride. The obtained fraction was analyzed by $^{29}$Si-NMR in order to determine the content of Si-bonded methacryloxy-functional organosilicon impurity compounds.

TABLE 3

| chemical shift | content (mol %) |
|---|---|
| 23.7 ppm | 0.23 |
| 19.4 ppm | 0.16 |

The content of each impurity was substantially higher than in Example 1 as indicated in Table 3.

Application Example 1

Measurement by gel permeation chromatography (GPC) was first run on a polydimethylsiloxane endblocked with silanol at a single terminal (measured hydroxyl content= 0.187 weight %). While cooling with water, 0.91 g (4.13 mmol) of the methacryloxypropyldimethylchlorosilane synthesized and distillatively purified as described in Example 1 was added dropwise to a mixture of 30 g (3.3 mmol) of the above-described polysiloxane, 0.45 g (6.13 mmol) of diethylamine, and 30 g of toluene. The completion of this addition was followed by stirring at room temperature for 3 hours and then methoxylation of the excess chlorosilane by the addition of 0.13 g (4.13 mmol) of methanol and stirring for 30 minutes at room temperature. The salt by-product was filtered off and the low boilers were distilled from the filtrate by heating under reduced pressure. Sterilizing filtration of the precipitated salt then yielded a colorless and transparent polydimethylsiloxane endblocked with methacryloxy at a single terminal. This material was again analyzed by GPC. The shape of the GPC peak prior to reaction with the methacryloxypropyidimethylchlorosilane was entirely unchanged from that after the reaction, indicating that dimerization of the polysiloxane had not occurred.

Application Example 2

A reaction was run as described in Application Example 1, but in this case using the methacryloxypropyldimethylchlorosilane distillatively purified as described in Comparative Example 1. When GPC measurement was run on the resulting polydimethylsiloxane endblocked with methacryloxy at a single terminal, the presence of a shoulder on the high molecular weight side indicated that dimerization of the polysiloxane had occurred as a side reaction.

That which is claimed is:

1. A method for preparing high-purity methacryloxypropyldimethylchlorosilane, said method comprising mixing (A) a methacryloxypropyldimethylchlorosilane which contains at least one Si-bonded methacryloxy-functional organosilicon compound as an impurity with (B) an inorganic chloride selected from the group consisting of thionyl chloride, phosphoryl chloride, phosphorus pentachloride, phosphorus trichloride, boron trichloride and mixtures of two or more of the preceding, reacting said inorganic chloride with said Si-bonded methacryloxy- functional organosilicon compound and thereafter isolating the methacryloxypropyldimethylchlorosilane.

2. The method according to claim 1, wherein said Si-bonded methacryloxy-functional organosilicon impurity is at least one compound having a formula selected from the group consisting of

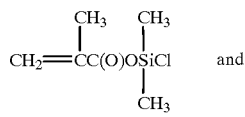
and

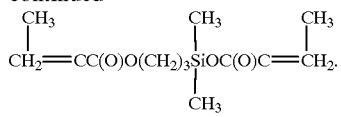

3. The method according to claim 1, wherein at least one equivalent of said inorganic chloride is used for each equivalent of said Si- bonded methacryloxy-functional organosilicon compound.

4. The method according to claim 1, wherein the reaction between said inorganic chloride and said Si-bonded methacryloxy-functional organosilicon compound takes place in the presence of an solvent.

5. The method according to claim 1, wherein the reaction between said inorganic chloride and said Si-bonded methacryloxy-functional organosilicon compound is carried out at a temperature of 50° C. to 200° C.

6. A purified methacryloxypropyldimethylchlorosilane prepared according to the method of claim 1.

7. A purified methacryloxypropyldimethylchlorosilane prepared according to the method of claim 2.

8. A purified methacryloxypropyldimethylchlorosilane prepared according to the method of claim 3.

9. A purified methacryloxypropyldimethylchlorosilane prepared according to the method of claim 4.

10. A purified methacryloxypropyldimethylchlorosilane prepared according to the method of claim 5.

* * * * *